(12) United States Patent
Buurlage

(10) Patent No.: US 11,666,421 B2
(45) Date of Patent: *Jun. 6, 2023

(54) DENTAL IMPLANT

(71) Applicant: LAKEVIEW INNOVATION LTD., Nidwalden (CH)

(72) Inventor: Thorsten Buurlage, Gorxheimertal (DE)

(73) Assignee: LAKEVIEW INNOVATION LTD., Nidwalden (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,966

(22) Filed: Oct. 4, 2018

(65) Prior Publication Data
US 2019/0029781 A1 Jan. 31, 2019

Related U.S. Application Data

(63) Continuation of application No. 14/085,587, filed on Nov. 20, 2013, now Pat. No. 10,117,730.

(30) Foreign Application Priority Data

Nov. 23, 2012 (EP) .................................... 12007906

(51) Int. Cl.
*A61C 8/00* (2006.01)
*A61C 13/00* (2006.01)
(Continued)

(52) U.S. Cl.
CPC .......... *A61C 8/0068* (2013.01); *A61C 8/0012* (2013.01); *A61C 8/0066* (2013.01);
(Continued)

(58) Field of Classification Search
CPC ....... A61C 8/00; A61C 8/0012; A61C 8/0013; A61C 8/0018; A61C 8/0022;
(Continued)

(56) References Cited

U.S. PATENT DOCUMENTS 4,636,216 A 1/1987 Tatum
5,152,687 A * 10/1992 Amino .................... A61C 8/005
433/176

(Continued)

FOREIGN PATENT DOCUMENTS

CN 102579143 A 7/2012
CN 102631247 A 8/2012
(Continued)

OTHER PUBLICATIONS

EP12007906.6, European Search Report, dated Apr. 24, 2013, 7 pgs.

*Primary Examiner* — Edward Moran
(74) *Attorney, Agent, or Firm* — Dickinson Wright PLLC

(57) ABSTRACT

Dental implant with a base body made of ceramic anchorable in a jawbone and an implant superstructure attachable to the base body using a screw, wherein in an assembled state of the dental implant, a threaded portion of the screw engages with an inner thread formed in a blind hole of the base body, wherein the implant superstructure is by the screw pressed against the base body and wherein the engagement between the threaded portion of the screw and the internal thread of the blind hole occurs only in a lower half of the base body facing away from the implant superstructure.

13 Claims, 1 Drawing Sheet

(51) Int. Cl.
  *A61C 13/20* (2006.01)
  *A61K 6/818* (2020.01)
(52) U.S. Cl.
  CPC ........ *A61C 13/0006* (2013.01); *A61C 13/206* (2013.01); *A61K 6/818* (2020.01)
(58) Field of Classification Search
  CPC ... A61C 8/0028; A61C 8/0037; A61C 8/0048; A61C 8/005; A61C 8/006; A61C 8/0063; A61C 8/0066; A61C 8/0068; A61C 8/0075; A61C 8/0078
  See application file for complete search history.

(56) References Cited

U.S. PATENT DOCUMENTS

| | | | |
|---|---|---|---|
| 5,286,195 A * | 2/1994 | Clostermann | A61C 8/0068 |
| | | | 433/172 |
| 5,316,476 A * | 5/1994 | Krauser | A61C 8/0018 |
| | | | 433/173 |
| 5,674,072 A | 10/1997 | Moser et al. | |
| 5,873,721 A | 2/1999 | Willoughby | |
| 6,655,961 B2 | 12/2003 | Cottrell | |
| 6,743,018 B1 | 6/2004 | Morrow | |
| 7,198,488 B2 | 4/2007 | Lang et al. | |
| 8,057,230 B1 | 11/2011 | Folsom, Jr. | |
| 2003/0120279 A1 | 6/2003 | Hansson | |
| 2009/0011384 A1 | 1/2009 | Collins et al. | |
| 2010/0247738 A1 | 9/2010 | Suh et al. | |
| 2012/0237899 A1 | 9/2012 | Holmstrom et al. | |

FOREIGN PATENT DOCUMENTS

| | | |
|---|---|---|
| DE | 19815719 C1 | 1/2000 |
| DE | 202008014591 U1 | 3/2009 |
| EP | 2025303 A1 | 2/2009 |
| EP | 2168530 A1 | 3/2010 |
| FR | 2945205 A1 | 11/2010 |
| JP | 09-066065 A | 3/1997 |
| JP | 2002-520119 A | 7/2002 |
| JP | 2010-220700 A | 10/2010 |
| JP | 2011-527917 A | 11/2011 |
| WO | 2007031562 A2 | 3/2007 |
| WO | 2010/006740 A2 | 1/2010 |
| WO | 2010106777 A1 | 9/2010 |

* cited by examiner

DENTAL IMPLANT

CROSS-REFERENCE

This application is a continuation of U.S. patent application Ser. No. 14/085,587, filed Nov. 20, 2013, which claims benefit of the filing date of EP12007906.6, filed Nov. 23, 2012, the entire contents of which are incorporated herein by reference for all purposes.

BACKGROUND

1. Field

The invention relates to a dental implant with a base body made of ceramic anchorable in a jawbone and an implant superstructure attachable to the base body using a screw, wherein in an assembled state of the dental implant, a threaded portion of the screw engages with an internal thread formed in a blind hole of the base body, and wherein the implant superstructure is by the screw pressed against the base body.

2. Description of Related Art

Such dental implants are already known from prior art. Tightening the screw results in stresses in the material of the base body and the implant superstructure. High stresses upon the ceramic used arise in the tightened state of the screw, both in the bearing areas between the base body and the implant superstructure as well as around the internal thread with which the thread flanks of the screw engage. The screw connection generates shear and tensile stresses that are particularly harmful for ceramic materials. Consequently, the ceramic material, being stable against compressive forces but unstable against tensile forces, is frequently overstressed. When tightening the screw, the ceramic material can in the bearing area between the base body and the implant superstructure suffer an incipient crack or even break.

Exemplary of such prior art is EP 2 168 530 A1 which discloses a ceramic implant comprising metallic coatings in an implant body, which are applied on the internal thread. Such a metal layer is also applied at a bevel at one end of the base body on which an implant superstructure bears in order to better absorb shear and tensile stresses. Such metallic inserts or coatings, however, must be applied in complex processes onto the ceramic base material and are therefore very expensive. The portion of the screw being in engagement with the internal thread is furthermore arranged in the upper part of the base body, whereas the lower portion of the base body is designed as a solid body. Therefore, the stresses arising when tightening the screw are concentrated on the upper portion of the base body, whereas no stresses prevail in the lower portion of the implant body. A multi-axial stress state comprising tensile and shear forces is therefore concentrated in this portion of the bearing area between the base body and the implant superstructure and the area around the internal thread. At the same time, the stresses are distributed very inhomogeneously over the entire length of the base body.

SUMMARY

The object of the present invention is to provide a dental implant that can be fabricated at low costs and comprises optimized transmission of forces for ceramic materials.

This object is achieved according to the invention in that the engagement between the threaded portion of the screw and the internal thread of the hole occurs only in a lower half of the base body facing away from the implant superstructure, said lower half extending over half the length of the base body.

This design has the effect that the stresses generated are homogeneously distributed over the entire length of the base body. Furthermore, the internal thread, into which the stresses are introduced directly via the screw, is located far away from the contact area with the implant superstructure, deep at the base of the base body. Due to this large distance between the bearing area and the portion of the internal thread engaging with the screw, tensile and shear stresses are largely avoided in the upper half in the bearing area between the base body and the implant superstructure. Instead, predominantly compressive stresses occur in this area, which can be much better absorbed by the ceramic material. The bearing area, frequently being thin-walled for space reasons, between the base body and the implant superstructure is greatly relieved of loads and the introduction of the screw stresses at the internal thread of the base body occurs in the more massive lower part of the base body. Consequently, the tendency to develop cracks is reduced and ease of assembly is increased. Additional reinforcement of the ceramic material, such as metal coatings in the bearing area and the internal thread, is no longer necessary, whereby the manufacturing cost of dental implants can be substantially reduced. It is even possible to fabricate the base body and the implant superstructure completely from ceramic without additional coatings, which again reduces manufacturing costs. Tensile stresses therefore occur mainly in the screw. Screws made of metal are particularly suitable for this, which in turn are cheap to produce.

Advantageous embodiments are claimed in the dependent claims and explained below.

It is according to a first embodiment of the invention of advantage, if the internal thread over its entire length extends only in the lower half of the base body. It is thereby not necessary to apply a thread over the entire length of the blind hole of the base body, whereby manufacturing costs are reduced. And shear stresses are then limited only to the lower part.

In a further embodiment of the invention, it is also advantageous if the length of the blind hole amounts to at least 80%, preferably to at least 90% of the total length of the base body. The entire length of the base body is thereby used most effectively for the transmission of the screw tension.

If in a further embodiment of the invention the blind hole bore, subsequent to the internal thread in the direction of the implant superstructure, is embodied as a fit bore, wherein there is a clearance fit with very little play or a transition fit between the fit bore and a shank of the screw, then a simple support is provided in the transverse direction to the longitudinal axis of the screw. Shear forces are thereby easily supported by the screw shank.

It is also advantageous if the length of the fit bore is according to another embodiment of the invention greater than the length of the internal thread. This provides an optimal ratio between the side support in the transverse direction and the pressure reduction in the contact area.

According to a further embodiment of the invention, the implant superstructure bears against the base body at a bearing surface extending substantially perpendicular to the longitudinal axis of the screw. This has the advantage that the pressure forces being transmitted by the base body to the implant superstructure or vice versa press on a vertical surface, whereby stress by shear forces is avoided. An even more ceramic-friendly design is thereby provided.

According to an advantageous embodiment of the invention, it is also advantageous if the implant superstructure comprises an extension that is in the assembled state of the dental implant inserted into a recess of the base body. This ensures that the implant superstructure is thereby in a simple manner supported with regard to the base body in the radial direction. Radial displacement of these two parts relative to each other is thereby prevented.

It is also possible, according to an advantageous embodiment of the invention, to provide an anti-rotation form fit between the implant superstructure and the base body. Rotation of the implant superstructure relative to the base body is prevented, in particular when being screwed together, but also during use.

According to a further embodiment of the invention, it is advantageous if both the implant superstructure as well as the base body are made of ceramic, preferably of zirconium oxide. This has the advantage that a particularly strong structure of the dental implant is ensured.

If, according to a further advantageous embodiment, the implant superstructure and/or the base body are fabricated by powder-injection molding, then this enables particularly cost-effective fabrication of the dental implant. The internal thread can also be shaped already in the forming process using this method, which again reduces manufacturing costs.

The invention also provides a base body for a dental implant, which also provides the advantages of low manufacturing costs and positive stress distribution, and is universally employable for other implant superstructures.

The invention is explained below by means of the embodiments using the figures.

DETAILED DESCRIPTION OF SPECIFIC EMBODIMENTS

Figure 1:
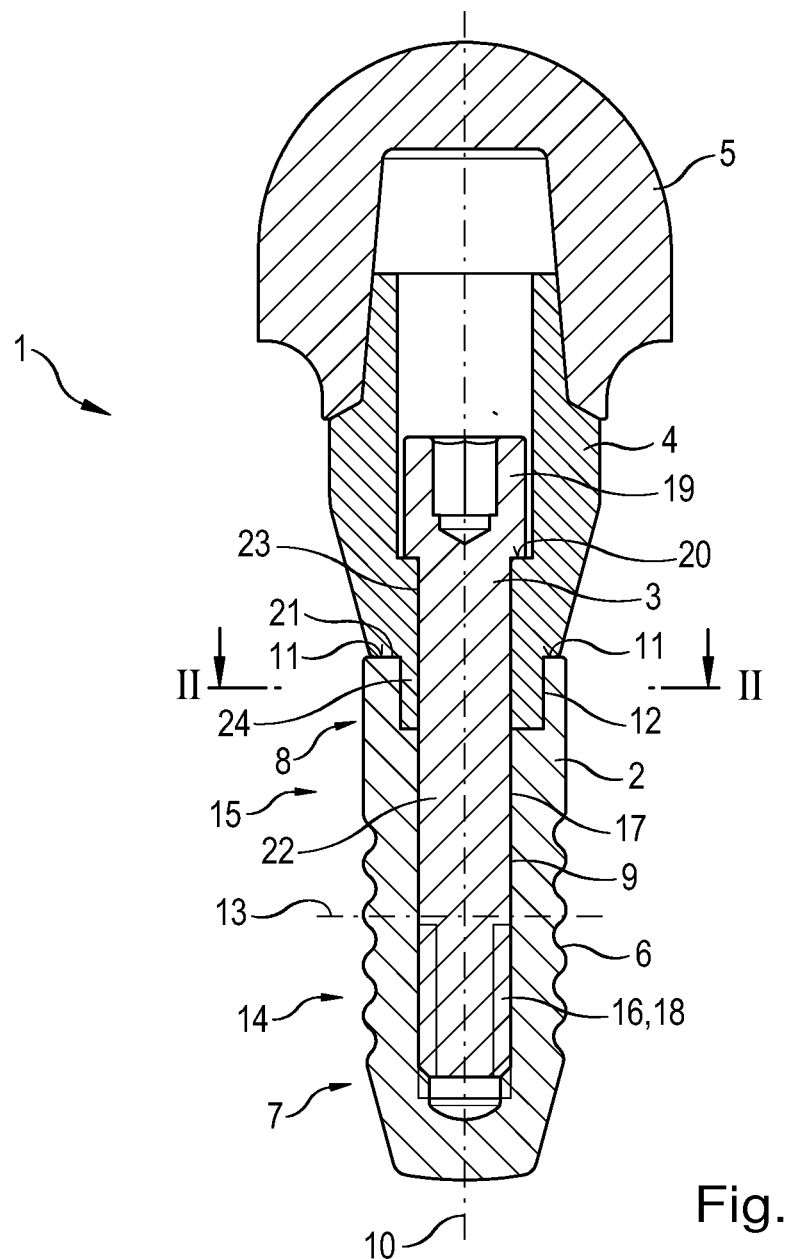
FIG. 1 shows a longitudinal section of the dental implant according to the invention along a longitudinal axis of a base body, anchored in the jaw bone of a patient.

The figures are merely schematic in nature and serve only to understand the invention. Same elements are denoted by the same reference numerals.

FIG. 1 shows a dental implant 1 comprising a base body 2 and an implant superstructure 4, which are fastened to each other using a screw 3. A dental prosthesis 5 can in turn be attached to the implant superstructure 4 in a known manner, for example, by cementing a dental crown.

The base body 2 is formed essentially cylindrically. For anchoring in a jawbone (presently not shown}, the base body 2 comprises an external thread 6 which is introduced into a jacket area of the base body 2. The base body 2 is screwed into the jawbone using this external thread 6. The jacket surface tapers conically towards the lower end portion 7 of the base body 2 being screwed into the jaw bone, whereby screwing the base body 2 into the jawbone is facilitated. A blind hole bore 9 is introduced into the base body 2 from the upper end portion 8 of the base body 2 facing away from the jaw bone and located opposite to the lower end portion 7. The blind hole bore 9 is arranged centered in the base body 2 and follows the longitudinal axis 10 of the base body 2 extending from the upper end portion 8 to the lower end portion 7 all the way into the lower end portion 8. The longitudinal axis 10 in the base body is therefore coaxial to the center axis of the blind hole bore 9.

Furthermore arranged at the upper end portion 8 of the base body 2 is a flat bearing surface 11 of the base body 2, which extends substantially perpendicular (90°) to the longitudinal axis 10 relative to the longitudinal axis 10. Between the blind hole bore 9 and the bearing surface 11, a recess 12 is provided in the base body 2 and co-acts with the counter profile of an extension 24 attached to the implant superstructure 4 as an anti-rotation lock, as is described in more detail below. The bearing surface 11 is the portion of the base body 2 protruding farthest upwardly towards the implant superstructure 4 in the direction of the longitudinal axis 10, and thereby forms a face side of the base body 2.

The distance in the direction of the longitudinal axis 10 of the base body 2 between the bearing surface 11 and the lower face side of the end portion 7 located opposite to it is hereinafter referred to as the "length" of the base body 10. This length is divided by an imaginary dividing plane 13 in two equal halves 14, 15. In a lower half 14 of the base body 2 facing the jawbone, an internal thread 16 is introduced into the blind hole bore 9. The lower half 14 and the upper half 15 therefore each extend across half of the length of the base body 2. The blind hole bore 9 extends so far into the lower half 14, that the length of the blind hole bore 9 amounts to at least 80%, particularly preferably at least 90%, most preferably at least 95% of the total length of the base body 2. The internal thread 16 itself is applied at an end of the blind hole bore 9 facing the lower end portion 7 and is formed only in the lower half 14 of the base body 2. Subsequent to the internal thread 16 in the direction of the implant superstructure 4, still in the lower half 14 of the base body 2, the internal thread 16 transitions into a fit bore 17 of the blind hole bore 9. This fit bore 17 extends end-to-end to the upper end portion of the base body 2 where the blind hole bore 9 transitions into the recess 12. The fit bore 17 is longer than the internal thread 16.

For attaching the implant superstructure 4, the screw 3 is inserted into the blind hole bore 9 so far until the threaded portion 18 of the screw 3 can be screwed into the internal thread 16. The screw 3 is in the assembled state screwed so far into the internal thread 16, that the screw head 19 bears against a screw head bearing 20 of the implant superstructure 4. The implant superstructure 4, in the assembled state bearing with a contact surface 21 against the bearing surface 11 of the base body 2, is in this area pressed firmly against the base body 2 by tightening the screw 3. A compression stress state therefore arises in this bearing area between the bearing surface 11 and the contact surface 21.

In this assembled state, the screw 3 is with its threaded portion 18 fully screwed into the internal thread 16. The threaded portion 18 therefore engages completely with the internal thread 16. Since the internal thread 16 is located entirely in the lower half 14 of the base body 2, the engaged portion of the screw 3 is therefore located entirely in the lower half 14 of the base body 2. A smooth shank 22 connects to the threaded portion 18 of the screw 3 and fits into the fit bore 17 of the base body 2 such that a clearance fit with very little play is given. The fit between the shank 22 and the fit bore 17 is preferably even configured as a transition fit, so that slight pressure must be applied to insert the screw 3 into the blind hole bore 9. The screw 3 can thereby just barely be moved in the fit bore 17 in the direction of the longitudinal axis 10, but bears with the outer surface of the shank 22 at least in part against the inner surface of the fit bore 17. The center axis of the screw 3 is in the assembled state preferably coaxial with the longitudinal axis 10 of the base body 2.

The shank 22 extends from the side of the screw head 19 contacting the screw head bearing 20 to the threaded portion 18. Also, in the implant superstructure 4, into which the shank 22 extends in part, same is guided in a fit bore 23 of the implant superstructure 4. The fit between the shank 22 and the fit bore 23 in the implant superstructure 4 is designed as a clearance fit with very little play. Therefore, both the implant superstructure 4 as well as of the base body 2 are supported in the transverse direction of the center axis of the screw 3, and, since this screw axis is coaxial with the longitudinal axis 10 of the base body 2, also the base body 2 is supported in the transverse direction of the longitudinal axis 10.

For radial fixation of the implant superstructure 4 relative to the base body 2, the implant superstructure 4 comprises an extension 24 that can be inserted into the recess 12 of the base body 2. Due to the insertion, the two components are in the assembled state radially mounted and thereby supported in the transverse direction of the longitudinal axis 10.

Figure 2:
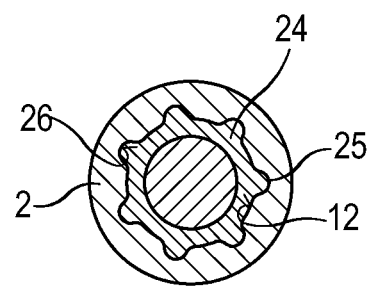
FIG. 2 shows a cross-section perpendicular to the longitudinal axis of the base body along the section line II marked in FIG. 1 as an illustrating of the anti-rotation lock.

As is particularly evident from FIG. 2, the extension 24 has a certain positive shape which is in the assembled state inserted into a negative shape of the recess 12. An anti-rotation lock of the base body 2 relative to the implant superstructure 4 about the longitudinal axis 10 is thereby ensured. The profile of the extension 24 in cross-section, i.e. transverse to the longitudinal axis 10, extends substantially ring-shaped, said ring shape comprising longitudinally extending bulges 25 at its outer side facing the recess 12. These bulges 25 are arranged on the outer side equidistantly around the center point of the extension 24 defined by the longitudinal axis 10. In this embodiment, seven bulges 25 are distributed uniformly around the center point, however, it is also possible to use a different number larger or smaller than seven of the bulges 25 arranged in parallel to each other. The side of the recess 12 facing the outer side of the extension 24 and subsequent to the blind hole bore 9 and the bearing surface 11 also extends at least in part parallel to the longitudinal axis 10 and has a negative shape that fits to the profile of the extension 24, such that the bulges 25 engage with grooves 26 of the recess 12. The engagement provides a support for the extension 24 at the recess 12. Any rotation of the base body 2 relative to the implant superstructure 4 is therefore not possible.

The implant superstructure 4, being designed essentially as a hollow cylinder, comprises a customary dental prosthesis 5 at one end facing away from the base body 2 which in the assembled state is cemented onto the implant superstructure 4.

The base body 2 is in this embodiment made entirely of ceramic, namely zirconium oxide, whereby the internal thread 16 at its thread flanks, which are in engagement with the threaded portion 18 of the screw 3, comprises this ceramic material. The implant superstructure 4 is also made entirely of ceramic material, namely zirconium oxide. Both the base body 2 as well as the implant superstructure 4 are manufactured by powder-injection molding, preferably using a ceramic injection molding (CIM) method.

The screw 3, or at least the shank 22 of the screw 3, is produced of a steel alloy, particularly preferably a titanium alloy.

For the assembly of the dental implant 1, the base body 2 is first screwed into the jawbone. If it is anchored in a sufficiently strongly manner, preferably already grown into the bone, then the implant superstructure 4 is subsequently attached by screwing-in the screw 3 into the bores of the implant superstructure 4 and the base body. The screw 3 is thereby put under tensile stress such that the implant superstructure 4 and the base body 2 are firmly pressed against each other. The bearing surface 12, formed perpendicular to the longitudinal axis 10, and the contact surface 21 bearing against it ensure surface contact of the implant superstructure 4 on the base body 2. Compressive stresses in the bearing area therefore occur mainly along the longitudinal axis 10 and parallel to the center axis of the screw 3. After the screw 3 is tightened, the dental prosthesis 5 formed as a crown or a bridge is then cemented onto the implant superstructure 4.

The invention claimed is:

1. Dental implant with
a base body made of ceramic and being anchorable in a jawbone, and having a bearing surface and a cylindrical blind hole with an internal thread formed in said blind hole,
an implant superstructure attachable to said base body, and contacting said bearing surface of said base body, and
a screw for attaching said implant superstructure to said base body,
wherein said bearing surface is located at a longitudinal end of said base body, facing away from an apical end of said base body, and wherein said bearing surface is a planar surface that extends substantially perpendicular to a longitudinal axis of said screw,
wherein in an assembled state of said dental implant, a threaded portion of said screw engages with said internal thread of said blind hole of said base body,
wherein in said assembled state said implant superstructure is pressed against said bearing surface of said base body by said screw,
wherein the length of the base body extends from said bearing surface to an apical end of the base body,
wherein said internal thread extends over its entire length only in the lower half of said base body facing away from said implant superstructure,
wherein said cylindrical blind hole comprises a bore, subsequent to said internal thread in the direction of said implant superstructure,
wherein the length of said bore is greater than the length of said internal thread, wherein the length of said blind hole amounts to at least 80% of the total length of said base body, and
wherein said engagement between said threaded portion of said screw and said internal thread of said blind hole occurs only in said lower half of said base body facing away from said implant superstructure.

2. Dental implant according to claim 1, wherein said implant superstructure comprises an extension that in said assembled state of the dental implant is inserted into a further recess of said base body, for providing an anti-rotation lock preventing rotation of the implant superstructure relative to the base body about a longitudinal axis of said base body.

3. Dental implant according to claim 1, wherein there is an anti-rotation form fit between said implant superstructure and said base body.

4. Dental implant according to claim 1, wherein said implant superstructure as well as said base body are both manufactured of ceramic material.

5. Dental implant according to claim 1, wherein said implant superstructure and/or said base body are manufactured by powder-injection molding methods.

6. Dental implant according to claim 1, wherein the length of said blind hole amounts to at least 90% of the total length of said base body.

7. Dental implant according to claim 4, wherein said ceramic material is zirconium oxide.

8. Dental implant according to claim 1, wherein a distance in the direction of a longitudinal axis of said base body between said bearing surface and an apical end of the base body defines a length of said base body, wherein said length is divided by an imaginary dividing plane into two halves of said base body, said two halves comprising an upper half facing toward said implant superstructure and said lower half of said base body facing away from said implant superstructure.

9. A base body for a dental implant,
wherein said base body is made of ceramic, is configured to be anchored in a jawbone, and has a bearing surface and a cylindrical blind hole with an internal thread formed in said blind hole,
wherein said bearing surface is located at a longitudinal end of said base body, facing away from an apical end of said base body, and wherein said bearing surface is a planar surface that extends substantially perpendicular to a longitudinal axis of said base body,
wherein the length of the base body extends from the bearing surface to the apical end of the base body,
wherein said base body is configured for attaching an implant superstructure to said base body by using a screw,
wherein in an assembled state of said dental implant, said implant superstructure contacts said bearing surface of the base body, and a threaded portion of said screw engages with said internal thread of said cylindrical blind hole of said base body,
wherein said implant superstructure in said assembled state is pressed against said bearing surface of said base body by said screw,
wherein said internal thread of said cylindrical blind hole is located only in a lower half of said base body facing away from said implant superstructure, and
wherein said cylindrical blind hole comprises a bore, subsequent to said internal thread in the direction of said implant superstructure,
wherein the length of said bore is greater than the length of said internal thread and wherein the length of said blind hole amounts to at least 80% of the total length of said base body.

10. The base body according to claim 9, wherein the length of said blind hole amounts to at least 90% of the total length of said base body.

11. The base body according to claim 9, wherein said ceramic material is zirconium oxide.

12. The base body according to claim 9, wherein a distance in the direction of the longitudinal axis of said base body between the bearing surface and an apical end of the base body defines a length of said base body, wherein said length is divided by an imaginary dividing plane into two halves of said base body, said two halves comprising an upper half facing toward said implant superstructure and said lower half of said base body facing away from said implant superstructure.

13. The base body according to claim 9, wherein said base body is manufactured by powder-injection molding methods.

* * * * *

UNITED STATES PATENT AND TRADEMARK OFFICE
CERTIFICATE OF CORRECTION

| | |
|---|---|
| PATENT NO. | : 11,666,421 B2 |
| APPLICATION NO. | : 16/151966 |
| DATED | : June 6, 2023 |
| INVENTOR(S) | : Thorsten Buurlage |

It is certified that error appears in the above-identified patent and that said Letters Patent is hereby corrected as shown below:

On the Title Page

Please change the name of the Assignee as follows:
(73) Assignee: from "LAKEVIEW INNOVATION LTD., Nidwalden (CH)"

To: -- MAXON INTERNATIONAL AG SACHSELN (CH) --

Signed and Sealed this
Twenty-ninth Day of October, 2024

Katherine Kelly Vidal
*Director of the United States Patent and Trademark Office*